United States Patent [19]

Fancher et al.

[11] 4,361,439
[45] Nov. 30, 1982

[54] METHOD OF INCREASING THE YIELD OF LEGUMES UTILIZING CHLOROACETYL-AMINOACID ETHYL ESTERS

[75] Inventors: Llewellyn W. Fancher, New Castle; Francis H. Walker, Mill Valley, both of Calif.

[73] Assignee: Stauffer Chemical Company, Westport, Conn.

[21] Appl. No.: 296,599

[22] Filed: Aug. 26, 1981

[51] Int. Cl.$^3$ .................... A01N 37/46; C07C 103/50
[52] U.S. Cl. ........................................ 71/106; 560/172
[58] Field of Search .......................... 560/172; 71/106

[56] References Cited

U.S. PATENT DOCUMENTS

| | | | |
|---|---|---|---|
| 2,743,262 | 4/1956 | Coover | 560/172 |
| 3,525,765 | 8/1970 | Fancher | 71/106 |
| 4,054,668 | 10/1977 | Kirino | 560/172 |
| 4,055,663 | 10/1977 | Barer | 424/319 |

FOREIGN PATENT DOCUMENTS 690815  7/1964  Canada ............................. 560/172

OTHER PUBLICATIONS

Tada, J.C.S. Chem. Comm., pp. 1004–1005 (1979).
Lidert, Synthesis, pp. 322–324.
Otani, J. Pharm. Sci., pp. 520–526 (1978).
Fischer, Ber., 36, pp. 2106–2116 (1903).

*Primary Examiner*—Michael L. Shippen
*Attorney, Agent, or Firm*—Michael J. Bradley

[57] ABSTRACT

A method of increasing the yield of legumes (soybeans) utilizing a compound of the formula

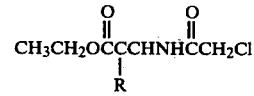

wherein R is selected from the group consisting of —H, —CH$_3$, —C$_2$H$_5$ and —C$_3$H$_7$.

8 Claims, No Drawings

METHOD OF INCREASING THE YIELD OF LEGUMES UTILIZING CHLOROACETYL-AMINOACID ETHYL ESTERS

BACKGROUND OF THE INVENTION

The present invention provides compounds and a method by which the yield of certain plants, particularly crop plants, can be improved by applying to such plants a yield-improving amount of certain chloroacetylaminoacid ethyl esters, described herein. The plants for which the present invention has been found especially useful are the legumes, e.g., soybeans, peas, peanuts and clover.

The application of the certain chloroacetylaminoacid ethyl esters improve the yield of legumes as much as about 25 percent. The term "yield" means dry weight of harvested pods of the legume crop plants. The yield per plant and the yield per acre is improved by application of the compound of this invention.

The term "soybean" includes both the determinate type (e.g. Bragg) which is grown in the southern United States, and the indeterminate type (e.g. Corsoy or Williams) which is grown in the northern United States and Canada. Generally, the determinate varieties of soybeans grow very little after flowering, if at all, and branch more profusely than indeterminate varieties. Indeterminate varieties increase their height by two to four times after flowering begins.

DESCRIPTION OF THE INVENTION

The novel compounds that are useful in the practice of this invention are chloroacetylaminoacid ethyl esters having the following structural formula

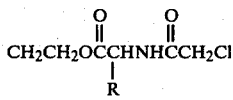

wherein R is H, —CH$_3$, —C$_2$H$_5$, or —C$_3$H$_7$.

The novel compounds of this invention can be prepared by the following general procedure.

1. Preparation of an amino acid ester

An aminoacid is suspended in an excess of the alcohol from which the ester is to be prepared and gaseous hydrogen chloride is passed into the mixture at 25°–65° C. An excess of hydrogen chloride of from 3 to 4–5 times the molar amount of aminoacid is used. The product, the aminoacid ester hydrochloride, can be used directly in step 2 or may optionally be converted to the free ester by reaction with ammonium hydroxide.

2. Preparation of a chloroacetylaminoacid ester

The ester prepared in step 1 is reacted with chloroacetylchloride at a temperature of from about −10° to +10° C. in a suitable solvent in the presence of a suitable base to produce the corresponding chloroacetylaminoacid ester. Solvents useful in this reaction include water, dichloromethane, and dichloroethane. Suitable bases include sodium bicarbonate, sodium carbonate, potassium carbonate, and sodium hydroxide. If the aminoacid is used in the form of its hydrochloride, a two-fold excess of base must be used.

EXAMPLE I (Compound No. 1)

Chloroacetyl glycine ethyl ester

Twenty-seven and nine-tenths grams (g) (0.2 mole) of glycine ethyl ester —HCl was combined with about 100 grams of ice in a reaction flask. Solid NaHCO$_3$ (33.6 g) (0.4 mole) was then added to this mixture followed by dropwise addition of 23.0 g (0.2 mole) of chloroacetyl chloride with stirring. The temperature of the reaction mixture was maintained between −10° and −5° C. by ice addition. The solid precipitate that formed was separated from the reaction mixture by filtration, washed with ice water and air dried. The yield was 15 g (41.7%) of a solid having a melting point of 60°–62° C. which was identified as the title compound by infrared (IR) spectroscopy analysis.

EXAMPLE II (Compound No. 2)

N-Chloroacetyl alanine ethyl ester

The procedure of C. S. Marvel and W. A. Noyes, *J. Amer. Chem. Soc.*, 42, 2265 (1920) was followed.

Thirty grams (0.34 mole) of alanine was suspended in 150 ml of ethyl alcohol in a reaction flask and anhydrous hydrogen chloride gas was passed into the mixture at an initial temperature of 25° C. Addition was continued until 50 g (1.4 moles) of gas had been added. The temperature rose to 65° C. over the course of the addition.

After addition was complete, the mixture was heated at reflux for 3.5 hours. During this time there was formation of a solid. Upon cooling, the solid separated and was removed by filtration to give 47.5 g of alanine ethyl ester hydrochloride (91% yield).

A solution of 7.2 g (0.064 mole) of chloroacetyl chloride in 20 ml dichloroethane was added dropwise at 0°–5° C. to a rapidly stirred mixture of 10 g (0.064 mole) of the DL-alanine ethyl ester, hydrochloride prepared above and 10.2 g of 50% aqueous sodium hydroxide (0.128 mole) in 80 ml dichloroethane. The mixture was allowed to come to room temperature after addition was complete. After standing 3 hours the product was isolated by washing with 50 ml of saturated salt solution, dried over magnesium sulfate, followed by evaporation of the solvent. The product, 8.0 g was a solid having a m.p. of 43°–47° C. and was identified by nuclear magnetic resonance (NMR) and infrared (IF) spectroscopy analysis as the title compound.

The following is a table of certain selected compounds that are useful in the practice of this invention. These compounds are preparable according to the general and specific procedure described herein. Compound numbers are assigned to each compound and are used throughout the remainder of this application.

TABLE I $$\underset{R}{CH_3CH_2O\overset{O}{\overset{\|}{C}}CHNH\overset{O}{\overset{\|}{C}}CH_2Cl}$$

| Compound Number | R | Melting Point |
|---|---|---|
| 1 | —H | 60–62° C. |

TABLE I-continued

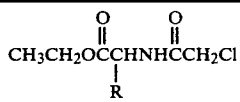

| Compound Number | R | Melting Point |
|---|---|---|
| 2 | —CH$_3$ | 43–47° C. |

EVALUATION TEST ON SOYBEANS

The purpose of this test is to evaluate compounds for soybean pod weight increase. Selected compounds of this invention are evaluated for such weight increase in the following manner.

Round fiber pots (6 inches in diameter) are filled with screened, sandy loam soil which has been fortified with 17-17-17 granular fertilizer to yield a soil mix having 150 parts per million (ppm) each of nitrogen, P$_2$O$_5$ and K$_2$O. Soybean seeds of either the determinate or indeterminate type are planted in the soil about 0.5 inches deep in a single row in sufficient number that 10–15 seedlings are obtained. After the seedlings have reached a unifoliate leaf stage they are thinned to four plants per pot.

Several such pots are retained as controls and other pots are treated with a candidate compound. The time of treatment of the four plants is between an early vegetative state and an early flowering state. The plants are treated with a compound by placing a pot on a linear spray table and spraying with 25 gallons per acre (235 liters per hectare) of an appropriate concentration of chemical compound to yield a treatment of ½, 1 or 2 pounds per acre (lb/A) (35, 70, or 140 grams per hectare). The compounds are dissolved in a 1:1 acetone-H$_2$O mixture containing 0.5 percent polyoxyethylene sorbitan monolaurate emulsifier prior to the treatment.

The treated plants are placed in a glasshouse and maintained at a temperature of approximately 70° F. at night and 80°–85° F. during the day. The plants are fertilized twice during the crop cycle with 1:1:1 ratio of a nitrogen, P$_2$O$_5$, K$_2$O fertilizer solution (3.4 grams nitrogen, P$_2$O$_5$, K$_2$O per liter of water). Normally 70 milliliters (ml) of this solution is added to each pot at each of the two fertilization times. Usually these fertilization times are at one and two months after seeding.

Control plants are also fertilized and maintained in the glasshouse in a like manner but are not treated with a candidate compound.

Evaluation is made after the plants have fully matured, i.e., when the leaves and pods have senesced. The term "pods" as used herein means pods with beans. The pods are removed from the treated plants, dried in a forced-air dryer at 120° F. to a constant weight, i.e., until all moisture is evaporated from the pods. Next, the dry weight of the pods is ascertained and compared to the dried weight of pods from an untreated plant.

The percent increase in pod weight is calculated and is reported in Table II.

TABLE II

| Compound Number | Treatment Rate lb/A | Percent Increase in Pod Dry Weight |
|---|---|---|
| 1 | ½ | 14 |
|   | 1 | 25 |
|   | 2 | 22 |

TABLE II-continued

| Compound Number | Treatment Rate lb/A | Percent Increase in Pod Dry Weight |
|---|---|---|
| 2 | 1 | 1 |
|   | 2 | 14 |

Application of the chloroacetylaminoacid ethyl esters of this invention may be made employing the procedures normally used for treatment of plants including dip or soak treatment of tubers, bulbs or cuttings, for example, as well as foliar, bark or stem or soil application. Preferably the compounds are applied in a post-emergence foliar application, more preferably the compounds are applied directly to the plant between about 4 weeks prior to flowering and about 2 weeks after flowering of the plant. The active ingredient may be utilized in diverse formulations, including the adjuvants and carriers normally employed for facilitating the dispersions of active ingredients for agricultural applications, recognizing the known fact that the formulations and mode of application of a chemical agent may affect its activity in any given application. Thus, chloroacetylaminoacid ethyl esters can be formulated as a solution or dispersion in a non-aqueous medium, as a powdery dust, as a wettable powder, as an emulsifiable concentrate, as a granule or as any of several other known types of formulations, depending upon the desired mode of application. These growth regulatory compositions may be applied as dusts, sprays, dips or granules in the sites in which growth regulation is desired. These formulations may contain as little as 0.0005% or as much as 95% or more by weight of active ingredient and applications may be at rates of about 1/32 to about 5 pounds per acre, preferably about 1/16 to about 2 pounds per acre.

Dusts are admixtures of the active ingredient with finely divided solids such as talc, attapulgite clay, kieselguhr and other organic and inorganic solids which act as dispersants and carriers for the regulant. These finely divided solids have an average particle size of less than 50 microns. A typical dust formulation useful herein is one containing 1.0 part of chloroacetylaminoacid ethyl ester and 99.0 parts of talc.

Wettable powders are in the form of finely divided particles which disperse readily in water or other dispersant. The wettable powder is ultimately applied to the plant either as a dry dust or as an emulsion in water or other liquid. Typical carriers for wettable powders include fuller's earth, kaolin clays, silicas, and other highly absorbent, wettable inorganic diluents. Wettable powders normally are prepared to contain about 5% to 80% of active ingredient, depending upon the absorbency of the carrier and usually also contain a small amount of a wetting, dispersing or emulsifying agent to facilitate dispersion.

Other useful formulations for plant applications are the emulsifiable concentrates which are homogeneous liquid or paste compositions which are dispersable in water or other dispersant and may consist entirely of chloroacetylaminoacid ethyl ester with a liquid or solid or emulsifying agent or may also contain a liquid carrier such as xylene, heavy aromatic naphthas, isophorone and other non-volatile organic solvents. For plant application, these concentrations are dispersed in water or other liquid carrier and normally applied as a spray to the area to be treated. The percentage of weight of the essential active ingredient may vary according to the manner in which the composition is to be applied, but in general, comprises 0.005% to 95% of active ingredient.

Other useful formulations include simple solutions of the active ingredient in a dispersant in which it is completely soluble at the desired concentration, such as acetone or other organic solvents. Granular formulations wherein the chemical agent is carried on relatively coarse particles are of particular utility for aerial distribution or for penetration of cover crop canopy. Pressurized sprays, typically aerosols wherein the active ingredient is dispersed in finely-divided form as a result of vaporization of low boiling dispersant solvent carrier such as the reons, may also be used.

Of course, the formulations, concentration and mode of application of chloroacetylaminoacid ethyl esters will be adapted to the particular plant and surrounding circumstances as is the case in all agronomic applications.

The active growth regulatory compound of this invention may be formulated and/or applied with other agricultural chemicals, such as insecticides, fungicides, nematocides, fertilizers and the like. In addition, combinations of chloroacetylaminoacid ethyl esters with certain plant hormones, such as native auxins, anti-auxins, giberellins and kinins, may produce enhanced growth regulatory effects.

What is claimed is:

1. A method of increasing the yield of legumes comprising applying thereto a yield-increasing amount of a compound of the formula

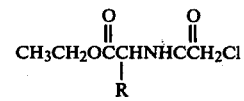

wherein R is selected from the group consisting of —H, —CH$_3$, —C$_2$H$_5$ and —C$_3$H$_7$.

2. The method of claim 1 wherein R is —H.

3. The method of claim 1 wherein R is —CH$_3$.

4. The method of claim 1 wherein the legume is soybeans.

5. The method of claim 1 wherein the yield-increasing amount of said compound is between about 1/32 to about 5 pounds per acre.

6. The method of claim 4 wherein the yield-increasing amount is applied between about 4 weeks prior to flowering of the soybeans plant and 2 weeks after said flowering.

7. The method of claim 6 wherein the yield-increasing amount of said compound is between about 1/16 to about 2 pounds per acre.

8. The method of claim 6 wherein the yield-increasing amount of said compound is between about 1/16 to about 2 pounds per acre.

* * * * *